United States Patent [19]
Peachey-Stoner

[11] Patent Number: 6,030,842
[45] Date of Patent: *Feb. 29, 2000

[54] METHOD, COMPOSITION AND DEVICE FOR THE DETERMINATION OF FREE HALOGENS IN AQUEOUS FLUIDS

[75] Inventor: Robert A. Peachey-Stoner, Chelan, Wash.

[73] Assignee: Environmental Test Systems, Inc., Elkhart, Ind.

[*] Notice: This patent issued on a continued prosecution application filed under 37 CFR 1.53(d), and is subject to the twenty year patent term provisions of 35 U.S.C. 154(a)(2).

[21] Appl. No.: 08/897,473

[22] Filed: Jul. 21, 1997

[51] Int. Cl.[7] .......................... G01N 33/00; G01N 21/02
[52] U.S. Cl. ........................... 436/125; 422/56; 422/61; 436/124; 436/164; 436/166; 436/169
[58] Field of Search ..................... 422/56, 61; 436/124, 436/125, 164, 166, 169

[56] References Cited

U.S. PATENT DOCUMENTS

| | | | |
|---|---|---|---|
| 3,233,974 | 2/1966 | Bradley . | |
| 3,811,840 | 5/1974 | Bauer et al. | 436/125 X |
| 4,092,115 | 5/1978 | Rupe et al. | 436/125 |
| 4,211,845 | 7/1980 | Genshaw et al. | 422/56 X |
| 4,290,773 | 9/1981 | Magers et al. | 436/169 |
| 4,340,669 | 7/1982 | Bauer | 422/56 X |
| 5,491,094 | 2/1996 | Ramana et al. | 436/125 |

FOREIGN PATENT DOCUMENTS 9712242   4/1997   WIPO .

OTHER PUBLICATIONS

L. Horner et al, *Chem. Abstr.* 1961, 55, 9330b.
Y. Misono et al. *J.Electroanal. Chem.* 1997,436,203–212.
J. Liang et al. *Junshi Yixue Kexueyuan Yuankan* 1993, 17, 266–270.
R. Bauer et al. *Anal. Chem.* 1971, 43, 421–425.
J. Lieberman et al, *Environ. Sci. Technol.* 1980, 14, 1395–1400.
P. Hapiot et al. *J. Electroanal. Chem.* 1993, 353, 225–235.
J. Liang et al. *Chem. Abstr.* 1994, 120,116 310b.

*Primary Examiner*—Arlen Soderquist
*Attorney, Agent, or Firm*—Zarley, McKee, Thomte, Voorhees & Sease

[57] ABSTRACT

A sensitive and convenient unitized method, reagent composition and test device is presented for the determination of free halogens in aqueous test fluid samples. The reagent composition basically consists of an azine type indicator material and an effective amount of a benzidine type catalytic material, the combination of two materials preferably being impregnated into a matrix material for ease of handling and use.

19 Claims, 3 Drawing Sheets

METHOD, COMPOSITION AND DEVICE FOR THE DETERMINATION OF FREE HALOGENS IN AQUEOUS FLUIDS

FIELD OF THE INVENTION

The present invention relates to a method, composition and test device for the determination of free halogens in aqueous fluids such as swimming pool and spa water and other aqueous environments where such chemicals are used as disinfectants and sanitizers. Although the present invention excels as an on-site or field test system, it can also advantageously be used in a laboratory setting.

BACKGROUND OF THE INVENTION

Halogens have for many years been used as sanitizers, disinfectants and cold chemical sterilants in a wide variety of settings and environments that require the attenuation or elimination of microorganisms that adversely affect human and animal health. Ideally, the evaluation of the sterility or safety of a particular aqueous fluid suggests that a representative sample of such fluid be actually tested for the presence, level and type of adverse or harmful microorganisms. This is, however, not always possible as such a testing methodology usually requires the use of time consuming microorganism culturing techniques or large and expensive laboratory instrumentation and equipment. A simpler technique involves a system for the determination of a safe and effective level of an anti-microorganism chemical such as a halogen in the subject fluid. Such test system should be rapid and easy to use in order to ensure that this level be achieved and maintained. This is usually done by utilizing a test kit or system which is adapted to the particular fluid or environment under scrutiny.

Of the many chemical disinfectants and cold chemical sterilants now in use in human and animal health care, by far the most common are the halogens. Even though there are some drawbacks to the use of halogens as disinfectants, the low cost and availability of such materials bring them to the forefront in the continuing battle to control harmful microorganisms in the many aqueous fluids we come into contact with in our everyday lives. In this regard, chlorine and particularly free chlorine and bromine are the chemicals of choice, especially in the recreational water area.

As indicated above, it is essential that a safe and effective level of the chemical being used as a disinfectant be maintained in the aqueous environment under consideration. This level is usually monitored by employing a test device or system which is reasonably specific for the material being used. In the case of halogens and particularly hypochlorous acid (HOCl), such materials, by their very nature, are very reactive substances and numerous test methodologies based on such reactivity have been developed over the years and sold to users as testing kits and devices. By far the most common methodology employs the use of oxidation/reduction indicator materials which change color in proportion to the concentration of halogen in the fluid being tested.

One complicating factor in the use and determination of chlorine and to some extent the other halogens in aqueous fluids resides in the fact that chlorine (in the form of hypochlorous acid) tends to react with ammonia and other nitrogenous materials to produce what is known as combined chlorine or chloramines. These materials are considered to be, at least in the case of chlorine, less effective as sanitizers or disinfectants. Hypochlorous acid is also known as free or available chlorine and after a portion of such material combines with nitrogenous substances, is known as combined chlorine.

The present invention accordingly relates to an easy to use, sensitive and effective test system for the detection of free or available halogens over a broad range of concentrations in aqueous fluids. As used herein, the term "halogen" includes chlorine, bromine and iodine when such materials are used alone or in combination with other sanitizers. The term "free" or "available" or "free available" halogen (chlorine) is defined as a measure of oxidizing capacity and is expressed in terms of the equivalent amount of elemental chlorine. The term "combined" or "combined available" chlorine is defined as chlorine which has reacted with ammonia or other nitrogenous compounds and finally the "free" and "combined available" chlorine, when present in the water, are collectively described as "total residual (available)" chlorine or simply "total" chlorine.

DESCRIPTION OF THE PRIOR ART

Available references relating to basic halogen chemistry and to the various methods of testing for halogens, both in the laboratory and on-site, are too numerous to completely list here. Excellent texts and monographs have been written on the subject, such as, for example, George Clifford White's work entitled "Handbook of Chlorination and Alternative Disinfectants", Third Edition, Van Nostrand Reinhold, 1992 and Seymour S. Block's text entitled "Disinfection, Sterilization, and Preservation", Fourth Edition, Lea and Febiger, 1991.

More specifically, however, the following patents and literature references are considered to be relevant prior art generally relating to the analysis or determination of analytes such as halogens, peroxides and other materials in aqueous fluids samples, which analyses create a visual or measurable response when the analyte (halogen) is contacted with an oxidation/reduction color forming indicator or mixture of such indicators:

1. U.S. Pat. No. 3,233,974 to Bradley (1966) discloses and claims azine-type materials which are alternative indicators to traditional benzidine materials used in dry reagent test devices for determining glucose in body fluids.
2. U.S. Pat. No. 4,092,115 to Rupe and Bauer (1978) discloses and claims a dry reagent test device for free chlorine using azine compounds such as syringaldazine.
3. U.S. Pat. No. 4,385,114 to Guthlein et al. (1983) discloses and claims the use of a multiple impregnation technique for the preparation of test strips for the determination of peroxides or peroxidative materials using a tetraalkylbenzidine compound as the indicator material.
4. U.S. Pat. No. 5,491,094 (1996) to Ramana et al. discloses and claims a test device and method for determining free chlorine in aqueous fluids using a tetraalkylbenzidine indicator, the novelty of such process being a pretreatment of the carrier or matrix to prevent chloramine interference.
6. Fenxi, Suliu et al. in the Chinese journal Fenxi Ceshi Tongbao, 1992, Vol. 11, ISS. 6, Pages 28–32 disclose a method for determining total chlorine using 3,3',5,5'tetramethylbenzidine.

SUMMARY OF THE INVENTION

The present invention involves the unexpected discovery that a catalytic or small amount of a benzidine type compound such as 3,3',5,5'-tetramethylbenzidine (TMB) can enhance or catalyze the response of an azine type indicator material such as syringaldazine to the presence of free halogen in an aqueous fluid. Such a combination of materials, i.e. TMB and azine, along with excipients and other additives such as buffers and color stabilizers can achieve the necessary color changes to enable the analyst to cover the broad range of concentrations encountered in the use of halogens as disinfectants in aqueous fluids. Preferably, the composition described immediately above is incorporated into or onto a matrix such as absorbent paper or a polymeric material and retained as a dry test device until used for the quantitative or semi-quantitative determination of halogen in the aqueous test fluid sample.

DESCRIPTION OF THE PREFERRED EMBODIMENTS

Figure 1:
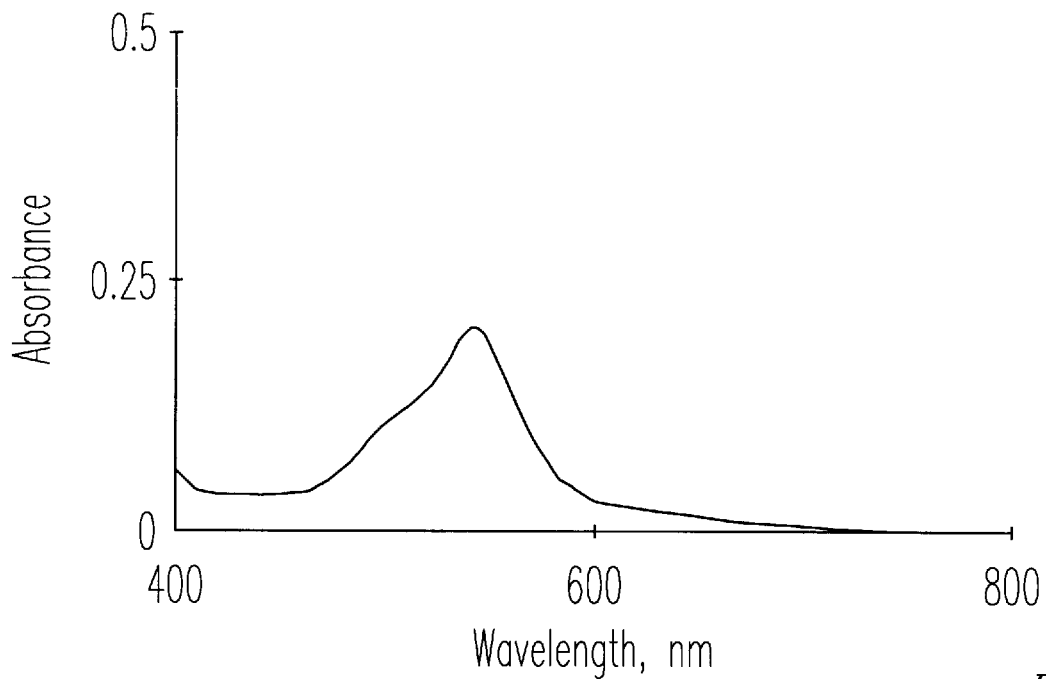
FIG. 1 is a spectrophotometric graph showing the response and color of an indicator solution of syringaldazine to the presence of free chlorine in an aqueous fluid.

The two basic ingredients of the test compositions of the present invention are the azine type indicator and the benzidine type catalyst. When using the term catalyst to describe the action of the benzidine type material in the present specification, the intention is to convey the fact that spectrophotometric data shows that this material does not itself contribute a color to the reaction between the test composition and the halogen analyte but rather enhances or accelerates the reaction of the indicator material to give a substantially more sensitive test system.

The chromogenic indicator material of the present test composition and device is an azine compound having the formula:

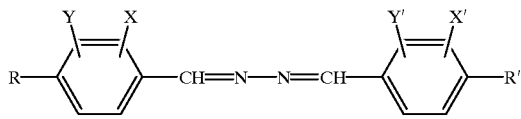

where R and R' are hydroxy or amino groups and X,X',Y and Y' are hydrogen, hydroxy, methyl, methoxy, ethyl and ethoxy groups and combinations thereof. Preferably, X,X',Y and Y' are meta substituted and are methoxy groups. Exemplary of such indicator materials which can be used in the present invention are syringaldazine; vanillinazine; 2,4,6, 2'4'6'hexahydroxy benzaldazine; 3,4,3', 4'tetrahydroxybenzaldazine; 3,3'-diethoxybenzaldazine; and the like.

The second basic ingredient in the present test composition is the benzidine type catalyst having the formula:

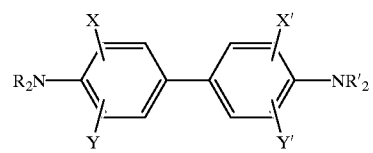

where X, X', Y and Y' and R and R' are hydrogen or an alkyl group of up to six carbon atoms and may be the same or different. Preferably the alkyl group contains four or less carbon atoms. Benzidine type compounds such as 3,3',5,5'-tetramethylbenzidine, o-tolidine, o-dianisidine, N,N'-tetramethylbenzidine, and the like may be used. 3,3',5,5'-tetramethylbenzidine is the preferable compound for use as the catalyst in the present composition.

For optimization purposes, it is preferable that the test composition contain a buffer to keep the test system within the pH range of about from 3.5 to 8.0. This is especially true in a recreational water test sample wherein the fluid itself contains little or no buffering capacity. Buffers such as phosphate, citrate, maleate and butanetetracarboxylate may be utilized.

As previously indicated, it is highly preferable that the composition of the present invention be incorporated in or on a matrix or carrier so that the test system may be stored and used as a dry reagent test device. Such a system can advantageously be used as a field test device by simply dipping the device into the fluid being tested and reading the color response on the surface of the matrix. Typical matrix materials comprise absorbent paper, both natural and synthetic, as well as woven and non-woven, and porous or nonporous polymeric materials whereby the test composition is mixed with the matrix material prior to its being solidified. Other devices may be prepared by attaching the test composition onto the surface of the carrier by chemical or physical methods. Depending on the test device design and use, the matrix structure may be flat or curved and the surface thereof may be smooth or rough.

It is also preferable that the matrix be utilized in conjunction with a handle means so that the resulting device may be easily presented to the fluid being tested. This is usually accomplished by attaching the impregnated matrix material to one end of an elongated strip of semi-rigid plastic sheet material. Common handle materials comprise polystyrene, polyethylene and so forth.

Other additives such as surfactants, thickeners, stabilizers, extenders, background dyestuffs and so forth may be included in the test composition as determined by the formulator and use of the device. The patent literature is replete with such materials and formulations.

Referring again to the basic components of the present invention, it will appreciated that there are a broad range of operable concentrations of materials which can be used. When employing a dry matrix such as absorbent paper to contain the test composition, the azine type indicator material is advantageously utilized in a concentration range in the impregnating solution of about from 75 mg/L to 300 mg/L and preferably in a range of about from 90 mg/L to 110 mg/L. When the concentrations of azine type material are used as indicated next above, it has been found that the benezidine type catalyst is ideally present in the test composition in a ratio of about one part catalyst to about from one to ten parts of indicator material and preferably from five to ten parts of indicator material. The concentration of buffer used depends upon the particular sample fluid being tested and may be adjusted by the skilled formulator according to the particular needs of the analytical process. Other components are used as needed and concentrations adjusted accordingly.

The compositions of the present invention are exemplified by the following experimental examples or models; however, the invention is not intended to be limited by or restricted to such examples.

Examples 1–7

In the examples that follow, stock solutions of the various ingredients were prepared as follows:

A. Buffer—A 0.4 M butanetetracarboxylic acid solution was prepared by dissolving butanetetracarboxylic acid in distilled water and adjusting the solution to the desired pH with sodium hydroxide.

B. Buffer—A 0.05 M butanetetracarboxylic acid solution was prepared by making 1 to 8 dilutions of the 0.4 M solution.

C. Chromogenic Indicator—A 0.5 mM syringaldazine solution was prepared by dissolving syringaldazine in reagent grade denatured ethyl alcohol.

D. Catalyst—A 0.1 mM 3,3',5,5'-tetramethylbenzidine (TMB) solution was prepared by dissolving this material in reagent grade denatured ethyl alcohol.

E. Free Chlorine Solution—A 100 ppm (1.4 mM) chlorine stock solution in water was prepared by appropriate dilution of commercial sodium hypochlorite. The concentration of this solution was confirmed by making a 1 to 100 dilution and performing amperometric titrations with standard phenylarsine oxide solutions. Working chlorine solutions were prepared by appropriate dilution of the stock solution with distilled water.

The reaction solutions were prepared as follows:

| Ingredient | Volume | Final Conc. |
| --- | --- | --- |
| 0.05 M buffer, pH 6.5 | 1.9 ml | 25 µM |
| 0.5 mM syringaldazine | 80 µL | 10.5 µM |
| 0.1 mM 3,3',5,5-TMB | 400 µL | 10.5 µM |
| chlorine solution | 1.0 mL | 3.7 µM |

In all the examples which follow (except for Example 8), the final solution contained 25 µM of buffer adjusted to a pH of 6.5. The final solvent concentration was 50/50 reagent ethyl alcohol and distilled water.

Example 1

This example shows the color response of syringaldazine alone to free chlorine. 10.5 µM syringaldazine was used and the chlorine concentration was 3.7 µM. The spectrophotometric curve resulting from this reaction is shown in FIG. 1.

Example 2

Figure 2:
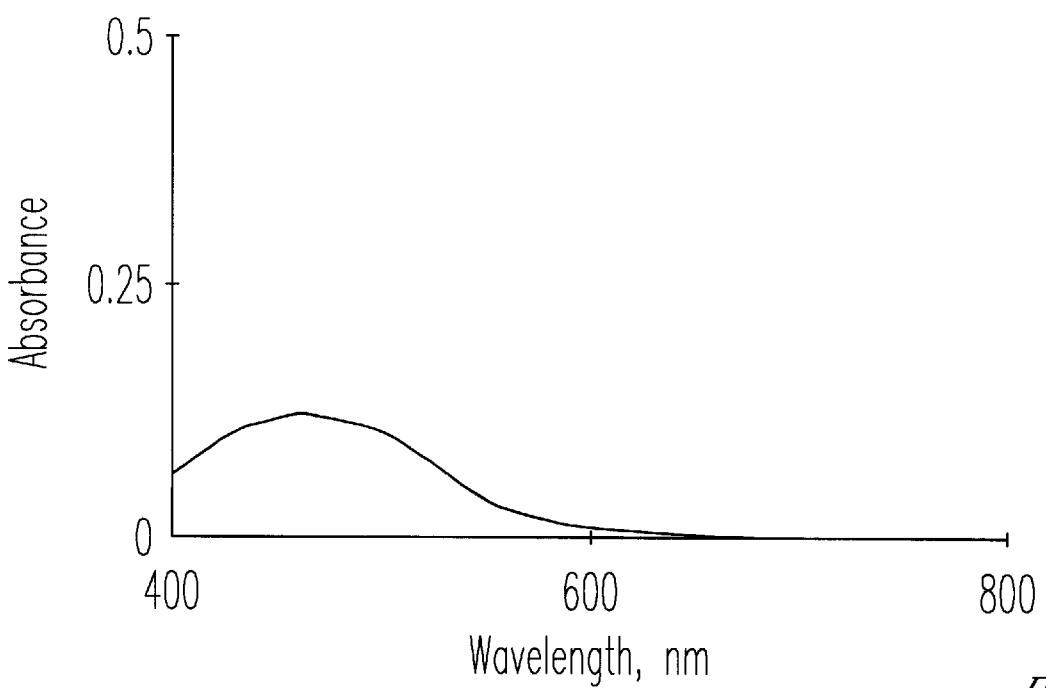
FIG. 2 is a spectrophotometric graph of the response of an indicator solution of 3,3',5,5'-tetramethylbenzidine (TMB) to the presence of the same solution of free chlorine as in FIG. 1.

This example shows the color response of 3,3',5,5'-TMB alone to free chlorine. 10.5 µM TMB was used and again the chlorine concentration was 3.7 µM. The spectrophotometric curve resulting from this reaction is shown in FIG. 2.

Example 3

Figure 3:
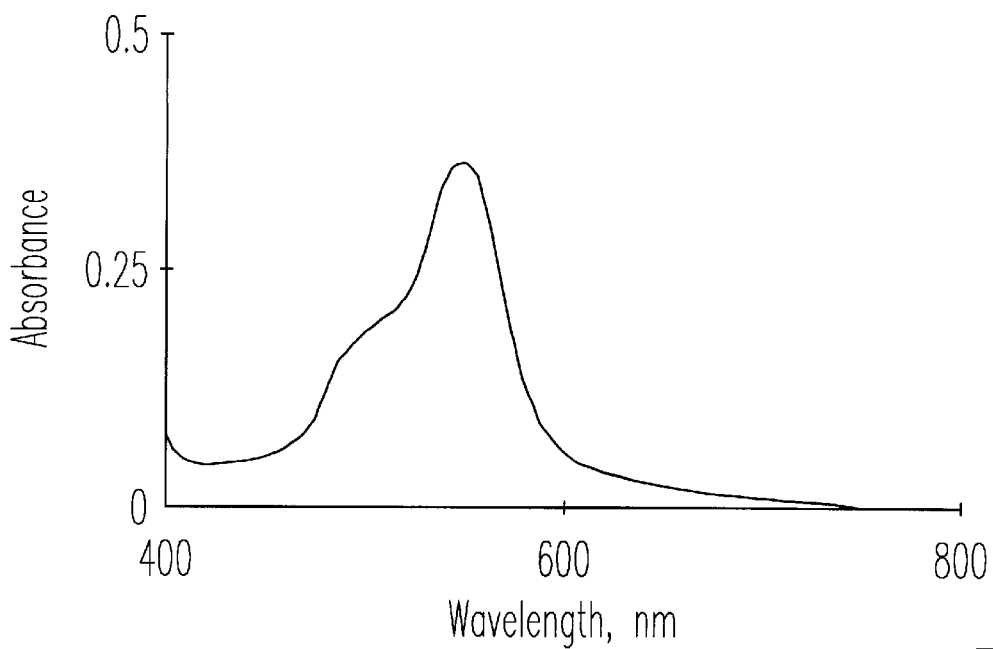
FIG. 3 is a spectrophotometric graph of the response of an indicator solution of syringaldazine to the presence of the same solution of free chlorine as in FIG. 1, except that the indicator solution contained a catalytic quantity of TMB.

This example shows the catalytic effect of TMB on the color response of the chromogenic indicator to the presence of free chlorine. 10.5 µM syringaldazine and 10.5 µM TMB were used and the concentration of free chlorine was again 3.7 µM. The spectrophotometric curve resulting from this reaction is shown in FIG. 3. It should be noted that the color response results from changes in the syringaldazine, and not in the TMB, and that the syringaldazine response is enhanced significantly by the presence of the TMB.

Example 4

Figure 4:
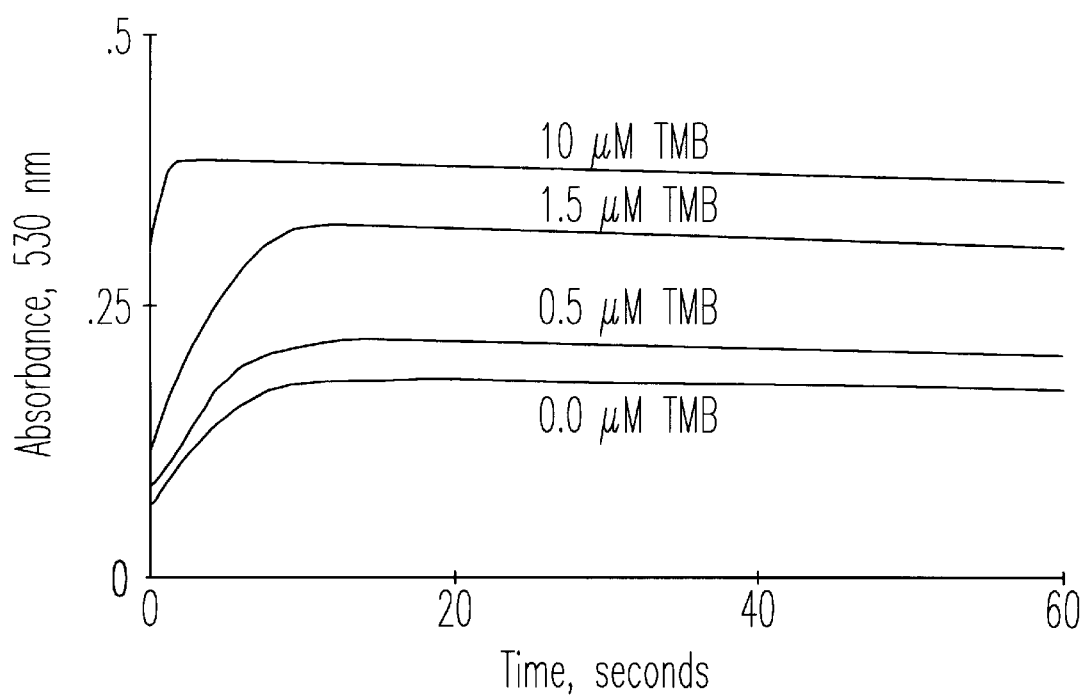
FIG. 4 is a graph showing the use of syringaldazine as a chromogenic indicator responding to free chlorine with varying concentrations of TMB as a catalyst for the reaction.

This example shows the response of the chromogenic indicator to free chlorine using varying amounts of catalyst. In this example, the syringaldazine concentration was 10.5 µM, the free chlorine was 3.7 µM and the TMB set at 0, 0.5, 1.5, and 10.5 µM. The results are shown in FIG. 4.

Examples 5–7

Figure 5:
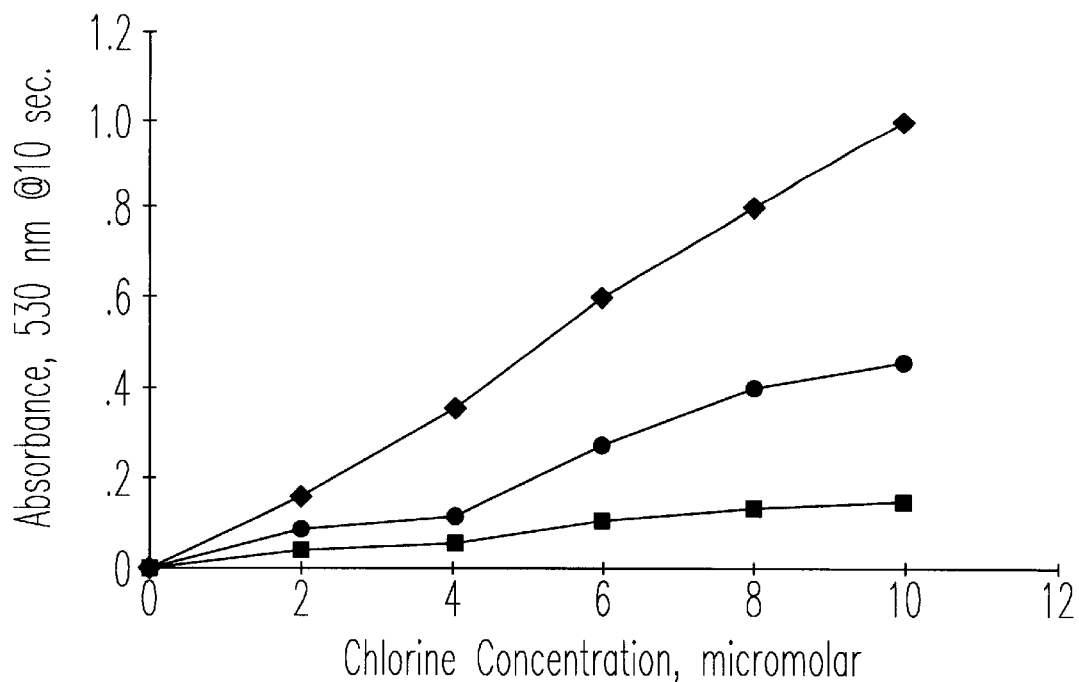
FIG. 5 is a graph showing the response of the use of syringaldazine plus a catalytic amount of TMB responding to various concentration solution of free chlorine.

These examples show the dose response of syringaldazine, TMB and syringaldazine plus TMB respectively to concentrations of free chlorine of 0, 2, 4, 6, 8, and 10 µM. The results are shown in FIG. 5.

Example 8

This example demonstrates the utilization of a matrix to contain the ingredients of the present invention in preparing a test device for field testing for free chlorine. 0.101 g of syringaldazine and 0.0156 g of 3,3',5,5'-TMB were dissolved in 0.5 L of reagent alcohol. 1.80 g of polyvinyl alcohol was dissolved in 0.5 L of hot distilled water, allowed to cool, 2.61 g of maleic acid added thereto and the mixture adjusted to a pH of 7.1. These two solutions were then combined and absorbent filter paper saturated therewith followed by oven drying. Small squares of this dried paper were attached to one end of elongated strips of polystyrene sheet material to form reagent strip test devices.

The resulting strip devices were momentarily dipped into concentrations of 0, 0.5, 1, 3, 5, and 10 ppm free chlorine and read in 15 seconds by comparing the color formed to a standard color chart containing printed color squares based on standardized color reactions. The color developed ranged from buff colored for 0 concentration free chlorine to deep lilac color for 10 ppm free chlorine with good color differentiation between chlorine concentrations.

What is claimed is:

1. A method for the determination of free halogen in aqueous solutions comprising:

contacting a test solution sample with a reagent composition consisting essentially of a chromogenic indicator material having the formula:

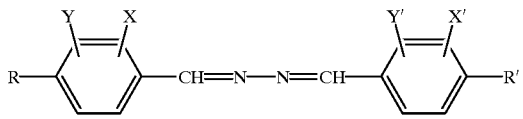

where R and R' are selected from the group consisting of hydroxy and amino groups and X,X',Y and Y' are selected from the group consisting of hydrogen, hydroxy, methyl, methoxy, ethyl and ethoxy groups and combinations thereof and;

an effective amount of a catalyst to enhance in a non-additive manner the response of the chromogenic indicator material to the presence of free halogen in the test solution sample, said catalyst having the formula:

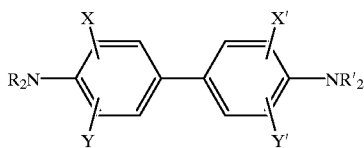

where X,X',Y,Y',R and R' are selected from the group consisting of hydrogen and alkyl groups of up to six carbon atoms, and a buffer to maintain the test composition and test solution sample in a pH range of about from 3.5 to 8.0; and, comparing the color response obtained to color responses from standardized solutions of free halogen and;

translating such comparison to the amount of free halogen in the test solution.

2. A method as in claim 1 wherein the catalyst is used in a ratio of about from one part catalyst to about one to ten parts chromogenic indicator.

3. A method as in claim 1 wherein the alkyl group contains not more than four carbon atoms.

4. A method as in claim 1 herein the chromogenic indicator is syringaldazine.

5. A method as in claim 1 wherein the catalyst is 3,3',5,5'-tetramethylbenzidine.

6. A method as in claim 1 wherein the chromogenic indicator is syringaldazine and the catalyst is 3,3',5,5',-tetramethylbenzidine.

7. A method as in claim 1 wherein the reagent composition is incorporated with a fluid absorbent matrix material and the matrix is contacted with the test solution sample.

8. A test composition for the determination of free halogen in aqueous fluid samples consisting essentially of:

a chromogenic indicator material having the formula:

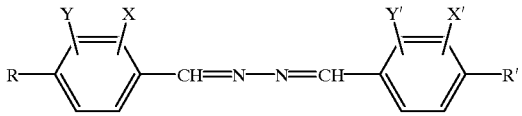

where R and R' are selected from the group consisting of hydroxy and amino groups and X,X',Y and Y' are selected from the group consisting of hydrogen, hydroxy, methyl, methoxy, ethyl and ethoxy groups and combinations thereof; and, an effective amount of a catalyst to enhance in a non-additive manner the response of the chromogenic indicator material, said catalyst having the formula:

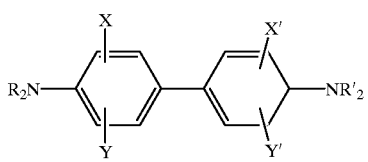

where X,X',Y,Y',R and R' are selected from the group consisting of hydrogen, and alkyl groups of up to six carbon atoms groups.

9. A test composition as in claim 8 wherein the catalyst is used in a ratio of about one part catalyst to about one to ten parts chromogenic indicator.

10. A test composition as in claim 8 which additionally contains a buffer for maintaining the test composition and test fluid sample at about a pH of from 3.5 to 8.0.

11. A test composition as in claim 8 wherein the alkyl group contains not more than four carbon atoms.

12. A test composition as in claim 8 wherein the chromogenic indicator is syringaldazine.

13. A test composition as in claim 8 wherein the catalyst is 3,3',5,5'-tetramethylbenzidine.

14. A test device for the determination of free halogens in aqueous test solutions consisting essentially of a matrix material incorporated with the dried residue of a test composition consisting essentially of the following constituents:

a chromogenic indicator material having the formula:

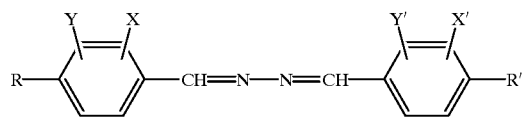

where R and R' are selected from the group consisting of hydroxy and amino groups and X,X',Y and Y' are selected from the group consisting of hydrogen, hydroxy, methyl, methoxy, ethyl and ethoxy groups and combinations thereof;

in combination with an effective amount of a catalyst to enhance in a non-additive manner the response of the chromogenic indicator material to the presence of free halogen in the test solution sample, said catalyst having the formula:

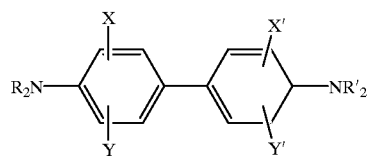

where X,X',Y,Y',R and R' are selected from the group consisting of hydrogen and alkyl groups of up to six carbon atoms groups; and, a buffer for maintaining the test composition in the matrix at a pH in the range of about 3.5 to 8.0 when the test device is contacted with the test solution sample.

15. A test device as in claim 14 wherein the catalyst is used in a ratio of about one part catalyst to about one to ten parts chromogenic indicator.

16. A test device as in claim 14 wherein the alkyl group contains not more than four carbon atoms.

17. A test device as in claim 14 wherein the chromogenic indicator is syringaldazine.

18. A test device as in claim 14 wherein the catalyst is 3,3',5,5'-tetramethylbenzidine.

19. A test device as in claim 14 wherein the matrix is absorbent paper.

* * * * *